(12) United States Patent
Yoo

(10) Patent No.: US 8,609,434 B2
(45) Date of Patent: Dec. 17, 2013

(54) BIO-DISC READING APPARATUS AND ASSAY METHOD USING SAME

(75) Inventor: Jae Chern Yoo, Gwacheon-si (KR)

(73) Assignee: Samsung Electronics Co., Ltd., Suwon-Si (KR)

( * ) Notice: Subject to any disclaimer, the term of this patent is extended or adjusted under 35 U.S.C. 154(b) by 687 days.

(21) Appl. No.: 12/735,729

(22) PCT Filed: Feb. 13, 2009

(86) PCT No.: PCT/KR2009/000691
§ 371 (c)(1),
(2), (4) Date: Aug. 12, 2010

(87) PCT Pub. No.: WO2009/102159
PCT Pub. Date: Aug. 20, 2009

(65) Prior Publication Data
US 2010/0312574 A1    Dec. 9, 2010

(30) Foreign Application Priority Data
Feb. 14, 2008    (KR) ........................ 10-2008-0014255

(51) Int. Cl.
| G01N 33/558 | (2006.01) |
| G01N 33/543 | (2006.01) |
| G01N 33/53  | (2006.01) |
| G01N 33/567 | (2006.01) |

(52) U.S. Cl.
USPC ............ 436/514; 436/518; 435/7.2; 435/7.21

(58) Field of Classification Search
None
See application file for complete search history.

(56) References Cited

U.S. PATENT DOCUMENTS

| 4,795,613 | A  | * | 1/1989  | Azuma et al. ................. 422/64 |
| 2002/0098528 | A1 | * | 7/2002  | Gordon et al. ............. 435/7.21 |
| 2003/0096324 | A1 | * | 5/2003  | Matveev et al. ............ 435/7.21 |
| 2003/0113925 | A1 | * | 6/2003  | Gordon et al. ................ 436/10 |
| 2003/0224457 | A1 | * | 12/2003 | Hurt et al. ..................... 435/7.2 |
| 2004/0264323 | A1 | * | 12/2004 | Worthington et al. ..... 369/47.27 |
| 2005/0014249 | A1 | * | 1/2005  | Staimer et al. ............. 435/287.2 |
| 2005/0272037 | A1 | * | 12/2005 | Garey et al. ..................... 435/6 |
| 2009/0163367 | A1 | * | 6/2009  | Yoo ................................. 506/7 |
| 2010/0121156 | A1 | * | 5/2010  | Yoo ............................... 600/300 |
| 2010/0234237 | A1 | * | 9/2010  | Yoo ................................. 506/9 |
| 2011/0256026 | A1 | * | 10/2011 | Kim et al. ................. 422/82.05 |

FOREIGN PATENT DOCUMENTS

| WO | WO 02/42498 | A2 | * | 5/2002 |
| WO | WO 03/080868 | A1 | * | 10/2003 |
| WO | WO 2007/001160 | | * | 1/2007 |

* cited by examiner

Primary Examiner — Shafiqul Haq
Assistant Examiner — Gary E Hollinden
(74) Attorney, Agent, or Firm — Staas & Halsey LLP

(57) ABSTRACT

Provided is a bio-disc reading apparatus for reading information including product authentication of a bio-disc and assay site of a bio-disc, and an assay method using same.

10 Claims, 12 Drawing Sheets

FIG. 1
QUIET ZONE　　　　　　　　　　　　　　　　　　　　QUIET ZONE
DATA　　CHECK CHARACTERS
START CHARACTERS　　　　　　　　　STOP CHARACTERS
FIG. 2

BIO-DISC READING APPARATUS AND ASSAY METHOD USING SAME

Cross Reference to Related Applications

This application claims the benefit under 35 U.S.C. Section 371, of PCT International Application No. PCT/KR2009/000691, filed Feb. 13, 2009, which claimed priority to Korean Application No. 10-2008-0014255, filed Feb. 14, 2008, the disclosures of which are hereby incorporated by reference.

BACKGROUND

1. Field

Embodiments of the present invention relate to a bio-disc reader to certify bio-disc products and read an assay site thereof and an assay method using the same.

2. Description of the Related Art

A barcode refers to a combination of black and white bar-shaped signs in the form of binary symbols, which enables data to be readily read by a computer and the same to be rapidly input. The barcode may be automatically read with an optical mark reader connected to a computer and input, stored or detected into the computer. Such a barcode is used for representation of the type of products in accordance with Universal Product Code (UPC) or point of sales systems (POSs) in stores such as supermarkets. The price of products input by barcodes may be displayed in a display device. For example, the barcodes are encoded in accordance with the UPC standard and are then interpreted with a reader including a barcode scanner and a decoder. When the barcode scanner reads barcodes, the corresponding codes are transferred to the decoder, are decoded by the decoder and are converted into recognizable information.

Generally, bio-discs include one or more assay sites in which a capture probe which is specifically biologically bound to samples is fixed and/or substances participating in biochemical reactions are stored. Bio-discs require, in addition to the barcode reader present therein, additional readers to read reaction results of the assay sites. This makes design of readers complicated and miniaturization suitable for the applications of bio-discs difficult.

SUMMARY

Therefore, it is one aspect of the present invention to provide a bio-disc reader to efficiently read information including product certification of bio-discs and assay sites using an image sensor and an assay method using the same.

Additional aspects of the invention will be set forth in part in the description which follows and, in part, will be obvious from the description, or may be learned by practice of the invention.

In accordance with one aspect of the present invention, provided is a bio-disc including: one or more assay sites to assay a biomaterial and perform biochemical reactions: a plurality of chambers to store fluids required for the biomaterial assay or biochemical assay; a plurality of channels to connect the chambers to one another and transfer fluids; a body to integrate the assay sites, the channels and the chambers; a barcode printed on the body or adhered thereto, a first thin-film circular magnet provided on the body to space-address the barcode; and a second thin-film circular magnet provided on the body to space-address the body.

In one embodiment, the first and second thin-film circular magnets may be arranged on the same radius as the bio-disc. The barcode may be a colored one-dimensional or two-dimensional barcode, or a horizontal barcode. The barcode may contain information such as operating protocol, product ID and expiration date of the bio-disc, and the type of diseases to be assayed and diagnosed. The barcode may include barcodes printed by a fluorescent ink. The fluorescent ink may be a transparent UV fluorescent ink.

In one embodiment, the bio-disc may further include a distinguishing device to distinguish the assay site from the barcode. The distinguishing device may be at least one selected from specific symbols, specific barcode patterns, specific color marks, specific holes, specific mechanical engravings, start characters and stop characters. The specific barcode pattern includes a horizontal barcode.

In one embodiment, the bio-disc may further include an ink chamber to store an ink to optically block the barcode, a barcode chamber including the barcode and a hydraulic burst valve interposed between the ink chamber and the barcode chamber.

In accordance with another aspect of the present invention, provided is a bio-disc reader including: a spindle motor to rotate the bio-disc; an image sensor to read the assay site and the barcode; a permanent magnet to space-address the first thin-film circular magnet and the second thin-film circular magnet; and a slider provided with the permanent magnets.

In one embodiment, the space-addressing the barcode or assay site may be carried out by radial direction search according to movement of the slider or azimuthal direction search through rotation of the spindle motor. The radial direction search may be carried out by repeatedly rotating and stopping a spindle motor after the slider is creased, or rotating a stepper motor mounted on a gear connected on the shaft of the spindle motor.

In accordance with another aspect of the present invention, provided is an assay method using the bio-disc according to the present invention including: loading the bio-disc on the bio-disc reader; searching barcodes by space-addressing the barcodes printed or adhered onto the bio-disc; reading the space-addressed barcodes; operating and analyzing the bio-disc according to a protocol corresponding to the read barcodes; searching assay sites by space-addressing the assay sites included in the bio-disc; reading the space-addressed barcodes; and displaying the assay results of assay sites.

The searching barcodes or searching assay sites may further include distinguishing the barcode from the assay sites. The distinguishing operation may further include repeating azimuthal direction searching, when an assay site is space-addressed during the barcode searching, or a barcode is space-addressed during the assay site searching. The azimuthal direction re-searching may include radially moving a slider toward the perimeter of the bio-disc; by-passing the assay site or barcode by rotation of the bio-disc; and moving the slider onto the original corresponding radius by radial direction searching. In addition, the distinguishing operation may be carried out by determining factors such as the distance of a test line, a control line and a reference line arranged in the form of a strip in the assay site, and positions, colors and color intensity thereof.

In one embodiment, the assay method may further include displaying statistical diagnosis and assay results of the assay site.

In one embodiment, the assay method may further include transmitting reading results of the assay site to a doctor through an Internet network; and remote-diagnosing a patient through remote-communication between a doctor and the patient.

In one embodiment, the assay method may further include reading the barcode and thereby determining whether the disc loaded on the bio-disc reader is a bio-disc or a general optical disc.

In one embodiment, the assay method may further include providing information of the bio-disc such as expiration date to a user by reading the barcode or informing the user that the bio-disc having a passed expiration date is unusable.

In one embodiment, the assay method may further include recognizing the barcode read by the image sensor, remote-transmitting information of the corresponding barcode via an internet network and supplying the authenticity of the bio-disc, product certification, product ID and product information from a server to a bio-disc reader.

In one embodiment, the operation for reading the barcode may further include reading the corresponding barcode to confirm efficiency, product information or product certification of bio-disc.

In accordance with another aspect of the present invention, provided is an assay method using the bio-disc according to the present invention including: loading the bio-disc on the bio-disc reader; searching barcodes printed or adhered onto the bio-disc; reading the searched barcodes; flowing an ink from the ink chamber to the barcode chamber to optically block the barcode; operating and analyzing the bio-disc according to a protocol corresponding to the read barcode; searching assay sites; reading the searched assay sites; and displaying diagnosis and assay results of assay sites.

In one embodiment, the assay method may further include informing a user that, when the bio-disc having the barcode optically blocked by the ink is re-loaded, the bio-disc is unusable, or automatically extracting the bio-disc from the bio-disc reader.

Hereinafter, the bio-disc reader and an assay method using the same will be illustrated in detail.

For example, the bio-disc may be applied to lab-on-a-chips utilizing ELISA/CLISA analysis methods, lab-on-a-chips utilizing rapid test methods; or thin-film devices to diagnose and detect a small amount of biological and/or chemical materials in fluids, such as lab-on-a-chips for food poisoning-causing bacteria assays, residual antibiotic assays, residual pesticide assays, assays of heavy metals in polluted water, genetically modified food tests, food allergy tests, contaminant assays, bacterial assays such as tests for $E.$ $coli.$ and $Salmonella$, paternity tests, meat type tests and origin region tests.

The residual pesticide comprises pesticide contained in vegetables or fruits, for example, the most-generally used organophosphorus and carbamate insecticides.

In one embodiment, the biomaterial may be at least one selected from DNA, oligonucleotides, RNA, PNA, ligands, receptors, antibodies, antibodies, milk, urine, saliva, hairs, crops, vegetable samples, meat samples, fish samples, bird samples, wastewater, livestock samples, food samples, food materials, stored foods, oral cells, tissue samples, semen, proteins or other biomaterials.

The term "food material" refers to a material for cooking foods and examples thereof including food materials for stew (jjigae), food materials for Kimchi and food materials for soups.

Upon urine assay, the bio-disc may perform leukocyte, blood, protein, nitrite, pH, specific gravity, glucose, ketone, ascorbic acid, urobilinogen and bilirubin assays.

For the thin-film chemical assay device, hair assay can more accurately measure historical record of nutriments and toxic substances including minerals accumulated, as compared to blood or urine assays.

The thin-film chemical assay device can accurately detect oversupply and lack of inorganic materials for a long time and the amount of toxic heavy metals.

The term "biochemical assay" used herein includes for example, assay of GOT, GPT, ALP, LDH, GGT, CPK, amylase, T-protein, albumin, glucose, T-cholesterol, triglycerides, T-bilirubin, D-bilirubin, BUN, creatinine, I. phosphorus, calcium, and uric acid in blood. The rapid test may use strips in which a variety of tumor markers or capture probes are fixed in the form of a line or spot on a porous membrane. The rapid test and ELISA methods may use a variety of tumor markers or capture probes fixed in the form of a line or spot on a porous membrane. The tumor markers include AFP, PSA, CEA, CA19-9, CA125, stomach cancer markers, breast cancer markers, lung cancer markers and A15-3. The capture probe may include capture probes to fix glutamine synthetase (GS), a specific marker for Alzheimer's. The capture probe may include capture probes to fix myocardial infarction markers such as myoglobin, CK-MB and Troponin I (TnI).

The rapid test includes fixing one or more markers or capture probes for AIDS, Alzheimer's disease, tumor markers, myocardial infarction, residual antibiotics, residual pesticides, allergy and breast cancer tests and assays for food poisoning-causing bacteria (ex. $E.$ $coli.$ and $Salmonella$) on the porous membrane and performing response tests using immunochromatography. Immunochromatography is a test method wherein immunochemistry is combined with chromatographic assay, which utilizes specific immune-response of antibody to antigens, color rendering and flowability of colloidal gold particles, and transfer of molecules on the porous membrane by capillary phenomenon. Immunochromatography is a convenient and rapid one-step method to perform processes including sample dilution, cleaning and color-rendering (chromogenesis) based on reaction of enzyme-complex with a substrate involved in conventional multi-step immunoanalysis methods. In addition, assay results obtained by the method can be read with an image sensor.

Considering thin film-type CDs and DVDs, standard compact discs can be formed from a 12 cm polycarbonate substrate, reflective metal layer and a protective lacquer coating. The format of CDs and DVDs may be in accordance with ISO 9660 industrial standard. The polycarbonate substrate is made of optical-quality transparent polycarbonate. A data layer in standard printed or bulk-copied CDs is a part of the polycarbonate substrate and the data is printed by a stamper in the form of a series of pits during injection molding. Polycarbonate molten during the injection molding process is injected into a mold at a high pressure and is then cooled to obtain polycarbonate in the form of the mold, the stamper or a mirror-image thereof, and pits showing binary data on the disc substrate are formed on the polycarbonate substrate. The stamping master may be a glass. Such a disc may be modified into a thin film analyzer to diagnose and detect a small amount of material in a fluid. In this case, channels to allow flow of fluids, chambers to store buffer solutions, and holes or valves, may be formed on the surface of the disc instead of the pits.

The disc is a thin-film assay device to diagnose and detect a small amount of material in a fluid, such as a thin film chemical assay device, which may be modified or reconstructed. In this case, the disc may include channels enabling flows of fluids, chambers to store a buffer solution, holes or valves provided on the surface of the disc during injection molding. The disc includes a circular disc having a diameter of 120 mm, 80 mm or 32 mm.

Hereinafter, a disc wherein the thin film chemical assay device is integrated in a conventional thin-film plastic body such as CDs or DVDs is referred to as a bio-disc.

The plastic body may be replaced by various materials such as silicon wafers. However, plastics as the bio-disc body are preferred, owing to economical efficiency, processability, and compatibility with conventional laser reflection-based detectors such as CD and DVD detectors. The substrate is composed of at least one selected from the group consisting of silicon wafers, polypropylene, polyacrylate, polyvinylalcohol, polyethylene, polymethyl methacrylate (PMMA), cyclic olefin copolymers (COCs) and polycarbonate.

In one embodiment, the assay site of the bio-disc includes labels to express reaction results using colorimetric information. The markers include fluorescent materials such as Cy3 or Cy5, gold conjugates, colorimetric particles or enzymes rendering colors by substrates.

In one embodiment, the recognition and reading of the bio-disc may be performed using an image sensor, and the difference between the black bar (black) and space bar (white) of the barcode may be translated and read into electrical signals by an image sensor. The barcodes may be applied to product certification such that they are printed or adhered onto bio-discs.

In one embodiment, the barcode may be in the form of a single bar or circle.

In one embodiment, the barcode may be a one-dimensional or two-dimensional barcode (or matrix code). The barcode may be a colored one-dimensional or two-dimensional barcode (or matrix code). When bars or matrices are expressed by various colors instead of black and white, they can contain more information and the image sensor can readily detect the colors.

The barcodes are generally divided into one-dimensional barcodes and two-dimensional barcodes. The one-dimensional barcodes are commonly in the form of long black bars and the two-dimensional barcodes are in the form of matrix or mosaic codes, in which corresponding information is contained in squares having a small size of about 20 mm. The one-dimensional barcodes can express information only widthwise depending on the thickness of bar lines, while the two-dimensional barcodes can contain information both widthwise and lengthwise. Accordingly, the two-dimensional barcodes can store 100 times to several hundred times more information than conventional one-dimensional barcodes (for example, about 20 bytes). In addition, although information present in two-dimensional barcodes is partially damaged, it can be considerably restored and can be read although a scanner is assessed in any direction. In particular, while one-dimensional barcodes supply only information associated with a database (DB), two-dimensional barcodes can serve as files and read information which is not connected to a database (DB). Two-dimensional codes are next-generation storage mediums which can store encoding and security and certification information and can prevent counterfeit and falsification or realize security.

In one embodiment, the two-dimensional barcodes may include information of bio-discs such as operating protocols, product ID and expiration date. The barcodes may be printed with a fluorescent ink, for example, transparent UV fluorescent ink to prevent duplication. The transparent UV fluorescent ink is ordinarily invisible with the naked eye, but emits light when exposed to UV radiation, which is well known in the art.

In one embodiment, the barcodes are adhered or printed onto the bio-disc to certify authenticity and provide product identification (ID) of the bio-disc.

In one embodiment, the bio-disc may further include a distinguishing device to distinguish the assay site from the barcode and the distinguishing device is selected from the group consisting of specific symbols, specific barcode patterns, specific color marks, specific holes, specific mechanical engravings, start characters, stop characters and combinations thereof. The specific color marks include color spots. The specific mechanical engravings are obtained by forming the plastic body into specific engravings and may be detected by an image sensor. The two-dimensional barcode may include operating protocol, product ID and expiration date of bio-discs and the types of diseases to be assayed and diagnosed.

In one embodiment, the thin-film circular magnets for space-addressing the assay sites and barcodes may be arranged on the same radius as the bio-disc. The thin-film circular magnets may be embedded in the body of the bio-disc.

In one embodiment, the present invention provides a bio-disc reader which loads a thin-film circular magnet for space-addressing the assay sites and barcodes on a bio-disc, analyzes information obtained by an image sensor to decide whether the space-addressed target is an assay site or barcode is, and performs product certification when the space-addressed target is a barcode, and reads an assay site when the space-addressed target is the assay site, and an assay method for using the same.

In one embodiment, the bio-disc reader further includes a slot, serving as an inlet and outlet of the bio-disc. In one embodiment, the bio-disc reader may further include a UV generator to read barcodes printed by a transparent UV fluorescent ink.

In one embodiment, the bio-disc reader may further include a slider equipped with a permanent magnet to enable movement to a specific position of the bio-disc; a spindle motor to rotate the bio-disc; and/or a slide motor to control movement of the slider.

The space-addressing may be carried out by radial direction search and azimuthal direction search.

The slider may perform azimuthal direction search by transferring the permanent magnet to the corresponding radius of assay sites and a barcode contained in the bio-disc. The radial direction search is a process for transferring the permanent magnet in a radial direction, which is carried out by transferring the slider from the center of the bio-disc to the radius r thereof. Then, the space-addressing the assay sites or barcode is completed by azimuthal direction search. The slider may be reversibly transferred from the center of the bio-disc by a gear connection with a slide motor or sled motor to the outside of the bio-disc, or from the outside of the bio-disc to the center of the bio-disc.

Hereinafter, two-dimensional positions of the bio-disc are expressed by the radius r and angle θ in the center of the circle. That is, positions in the bio-disc may be expressed by coordinates (r, θ). Hereinafter, the coordinates of barcodes refers to $(r_0, \theta_1)$ and the coordinates of assay sites refer to $(r_0, \theta_2)$.

In one embodiment, the barcodes and assay sites may be arranged on the identical radius $r_0$. The thin-film circular magnet for space-addressing the barcode is arranged on the coordinates $(r_0, \theta_1)$ of the bio-disc and the thin-film circular magnet for space-addressing the assay sites is arranged on the coordinates $(r_0, \theta_2)$. That is, the thin-film circular magnet for space-addressing the barcodes may be arranged on the same radius as the thin film circular magnet for space-addressing assay sites.

In one embodiment, the space-addressing may firstly perform radial direction search for moving the permanent magnet to the radius $r_0$ for arrangement of the image sensor and the barcodes or the image sensor and assay sites. The radial direction search is a process for moving the permanent magnet in a radial direction, which is carried out by moving the slider $r_0$ to a position spaced from the center of the bio-disc by a distance. Then, azimuthal direction search on the radius $r_0$ is required. The azimuthal direction search is carried out by rotating the bio-disc by repeatedly rotating and stopping the spindle motor while stopping the slider. When the permanent magnet of the slider corresponds to the thin-film circular magnet arranged on the radius $r_0$ through the repeated rotation of the spindle motor, the bio-disc cannot rotate due to attractive force therebetween and arrangement between the permanent magnet and the thin-film circular magnet may be carried out. As a result, arrangement between the image sensor and the barcode, or arrangement between the image sensor and the assay sites may be carried out and the image sensor distinguishes the barcodes from the assay sites. When the image sensor and the barcodes are arranged, and at the same time, the image sensor and assay sites are arranged, the arrangement between the image sensor and barcode may be formed by transferring the slider to the perimeter of the bio-disc in a radial direction and by-passing the assay sites through rotation of the spindle motor, and repeating the radial direction search and azimuthal direction search. In addition, when the image sensor and the assay sites are arranged, and at the same time, the image sensor and the barcodes are arranged, the arrangement between the image sensor and the assay sites may be formed by transferring the slider to the perimeter of the bio-disc in a radial direction and repeating the radial direction search and azimuthal direction search.

In one embodiment, rotation of the bio-disc in a radial direction for azimuthal direction search may be performed by rotating the step motor at a predetermined degree upon only azimuthal direction search on a gear connected on the shaft of the spindle motor.

In one embodiment, the bio-disc reader recognizes the barcode read by the image sensor and receives product information such as authentication, and product ID of the bio-disc from a server by remote-transmitting the corresponding barcode information over the Internet. The bio-disc reader recognizes the assay sites read by the image sensor and remote-transmits information of the assay sites over the Internet. The server may be a server provided by the manufacturer of the bio-disc. It is considered that the bio-disc is not genuine in the following two cases. For example, the bio-disc has no barcode or, if present, the codes are discordant. In the two cases, product ID information cannot be received from the server. In this case, the bio-disc reader may inform a user of an error massage through a voice or display means.

In one embodiment, the barcode search or assay site search may further include distinguishing the barcode from the assay site.

The distinguishing operation includes repeating azimuthal direction searching when the assay site is space-addressed during barcode search. That is, when the space-addressed during barcode search is an assay site, the azimuthal direction search is continued until the barcode is space-addressed. Accordingly, the azimuthal direction search includes: radially moving the slider to the perimeter of the bio-disc; by-passing the assay site by rotation of the bio-disc; and moving the slider onto the original corresponding radius by radial direction searching.

The distinguishing operation includes azimuthal direction re-searching when the barcode is space-addressed during assay site searching. That is, when a barcode is space-addressed during assay site searching, the azimuthal direction search is continued, until the barcode is space-addressed. Accordingly, the azimuthal direction re-searching includes: radially moving the slider to the perimeter of the bio-disc; by-passing the barcode by rotation of the bio-disc; and moving the slider onto the assay site by radial direction searching.

The thin-film circular magnets of the assay site and the barcodes are arranged on the identical radius, thus requiring distinguishing the assay site from the barcodes during azimuthal direction search. The operation for distinguishing the assay site from the barcode is carried out using at least one distinguishing means selected from the group consisting of specific symbols, specific barcode patterns, specific color marks, specific holes, specific mechanical engravings, start characters and stop characters.

In one embodiment, the bio-disc may further include a distinguishing device to distinguish the assay site from the barcode. The distinguishing device may be at least one selected from specific symbols, specific barcode patterns, specific color marks, specific holes, specific mechanical engravings, start characters and stop characters. The specific barcode pattern includes a horizontal barcode.

In one embodiment, the operation for distinguishing the barcode from the assay sites may be carried out by determining factors such as the distance between a test line, a control line and a reference line arranged in the form of a strip in the assay sites, and positions, colors and color intensity thereof.

In one embodiment, the distinguishing for the barcode from the assay sites further includes an ink chamber to optically block the barcodes. The barcodes blocked by the ink of the ink chamber may be readily distinguished from the assay sites.

In one embodiment, the assay method may further include displaying statistical diagnosis and assay results of the assay sites.

In one embodiment, the assay method may further include transmitting reading results of the assay site to a doctor through an internet network; and remote-diagnosing a patient through remote-communication between a doctor and the patient.

In one embodiment, the assay method may further include reading the barcode and thereby determining whether the disc loaded on the bio-disc reader is a bio-disc or a general optical disc. For example, when the disc is a bio-disc, product ID thereof can be detected by space-addressing the barcode, but the optical disc has no barcode. As a result, whether the disc is a bio-disc or an optical disc can be determined.

In one embodiment, the assay method may further include providing information of the bio-disc such as expiration date to a user by reading the barcode or informing the user that the bio-disc having a passed expiration date is unsuitable for diagnosis (or unusable). For example, the present date is compared with a manufacture date of the bio-disc based on the product ID to determine the possibility of diagnosis.

BRIEF DESCRIPTION OF THE DRAWINGS

These and/or other aspects of the invention will become apparent and more readily appreciated from the following description of the embodiments, taken in conjunction with the accompanying drawings of which:

FIGS. 1 and 2 illustrate configurations of a conventional barcode according to one embodiment;

DETAILED DESCRIPTION

Figure 3:
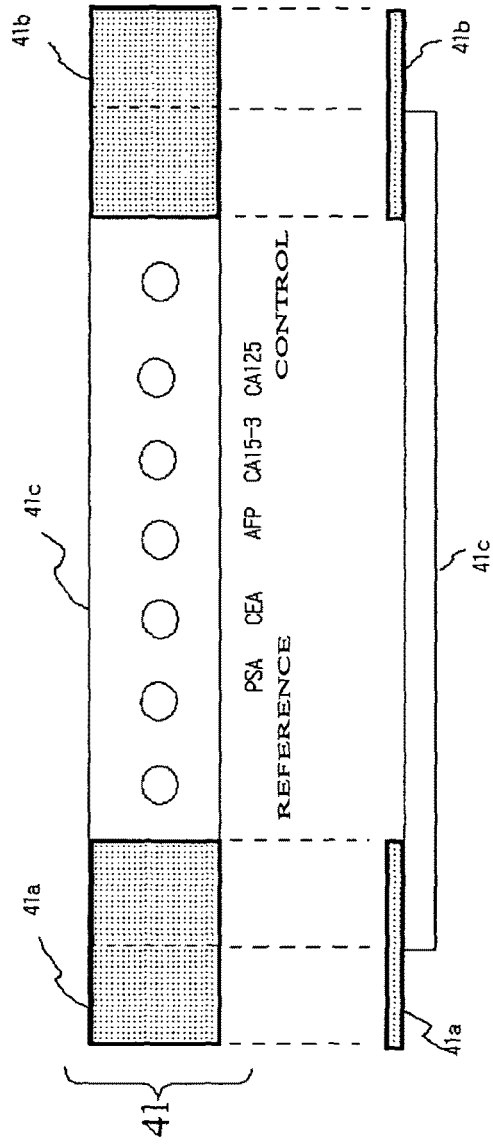
FIGS. 3 to 5 illustrate strips wherein various species of tumor markers are fixed in the form of a line or spot on a porous membrane according to one embodiment.

Reference will now be made in detail to the embodiments of the present invention, examples of which are illustrated in the accompanying drawings, wherein like reference numerals refer to like elements throughout.

FIGS. 1 and 2 illustrate configurations of a conventional barcode according to one embodiment.

FIG. 1 shows a one-dimensional barcode according to one embodiment. A conventional one-dimensional barcode is a representation of data, wherein zero (numeral) or specific symbols are encoded using a combination of thick or thin bars (black bars) and space bars (white bars) so that they can be readily optically read. In addition, a one-dimensional barcode includes about 150 types of code systems depending on the thickness of bars and the widths of spaces. A representation of barcodes according to respective code systems is referred to as a barcode symbology. In the barcode symbology, the space present in the start and end of the barcodes is referred to as a quiet zone, which indicates a blank present in front of start characters or a blank present in back of stop character, is essentially required to accurately define start and end of the barcodes and is designated in a size of 10 or more times higher than the most narrow element. The start characters are recorded in the most front of the barcodes, which provide information such as input direction of the data and types of barcodes to the barcode scanner. The stop characters indicate to the barcode scanner when the barcode symbols are terminated and enable the barcode scanner to read data in both directions. In addition, the barcode includes check characters which check accurate reading of messages and are thus applied to the fields requiring accuracy of information. The barcode symbols include information (including numerals, characters and symbols) which is visible by the naked eye, called "interpretation line", present in an upper or lower part of barcodes, which include manufacture codes and product category codes. Meanwhile, FIG. 2 shows various embodiments of a conventional two-dimensional barcode.

Figure 4:
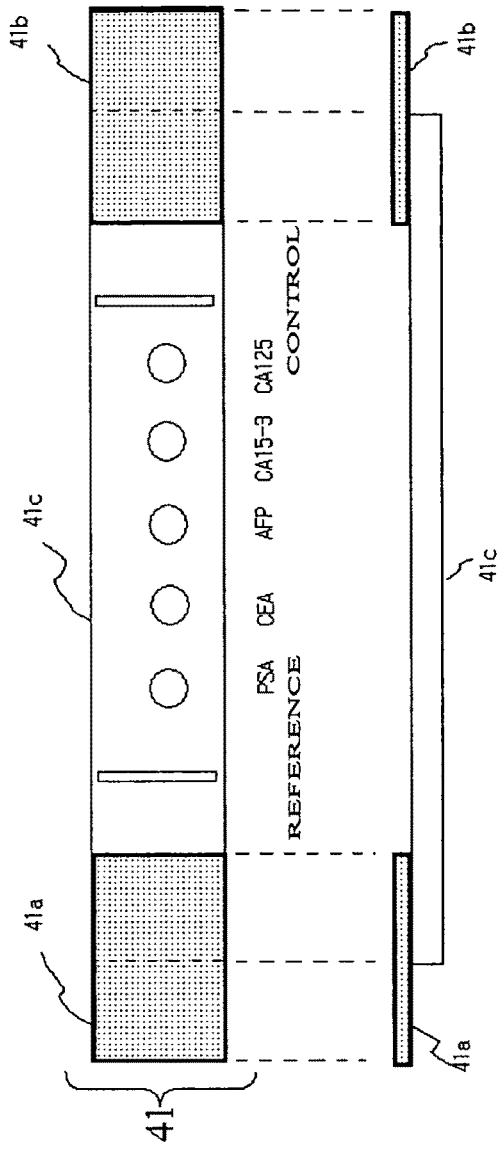
Figure 5:
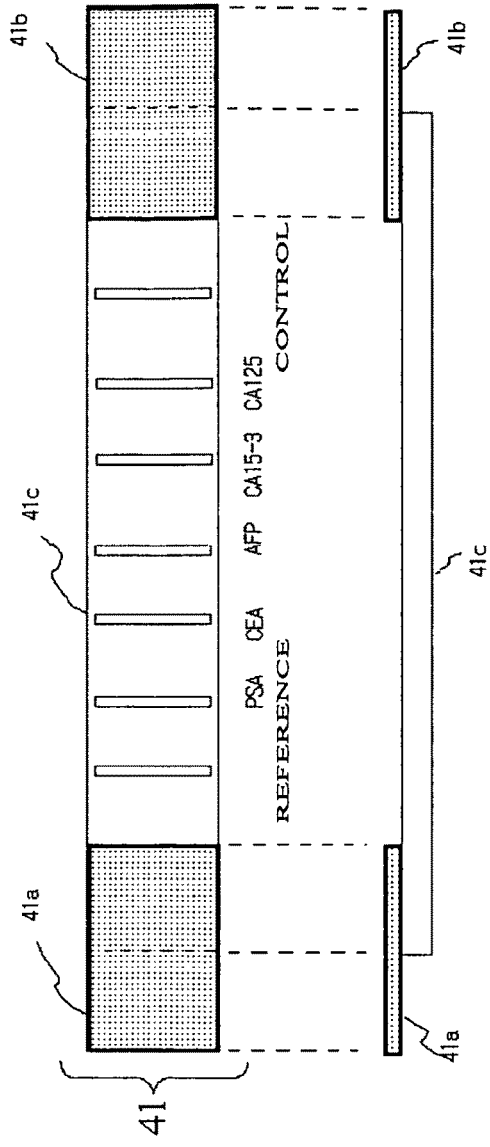

FIGS. 3 to 5 illustrate strips wherein various species of tumor markers are fixed in the form of a line or spot on the porous membrane according to one embodiment. Hereinafter, each of various species of tumor marker lines or spots is referred to as a test line. Reference numeral 41a is a conjugate pad, a sample pad, or a combination thereof and reference numeral 41b is an absorbent pad. Reference numeral 41c is a porous membrane. The conjugate pad may have a structure in which a gold conjugate, an enzyme-linked antibody or a label such as a fluorescent marker is deposited in a lyophilized form on a pad. The capture probe (for example, capture antibody) present on the porous membrane can fix the tumor markers. The tumor markers may be at least one selected from the group consisting of AFP, PSA, CEA, CA19-9, CA125 and A15-3. The capture probe can fix glutamine synthetase (GS), a specific marker for Alzheimer's. The capture probe can fix myocardial infarction antibody markers such as myoglobin, CK-MB and Troponin I (TnI). Also, one embodiment includes fixing one or more markers or capture probes for AIDS, myocardial infarction, residual antibiotics, residual pesticides, allergy and breast cancer tests on the porous membrane 41c and performing response tests using immunochromatography. Also, the capture antibody further includes, in addition to tumor markers, antibodies for reference and control lines. Plural reference lines may be present. The reaction concentration of the reference line may be a cutoff value to enable easy detection of negative or positive responses. For example, the cutoff value of the reference line may be selected from 3 ng/ml, 4 ng/ml, 10 ng/ml, 20 ng/ml, 30 ng/ml, 40 ng/ml and 50 ng/ml.

One embodiment comprises qualitative or quantitative analysis based on the difference in reaction intensity between the reference line and the test line. One embodiment comprises qualitative or quantitative analysis based on the difference in reaction intensity between the background and the test line. One embodiment comprises qualitative or quantitative analysis performed by determining reaction intensity of the test line through a linear function of reaction intensity formed by a plurality of reference lines. One embodiment comprises qualitative or quantitative analysis performed by determining reaction intensity of the test line through a linear function of reaction intensity formed by the reference line and the control line.

The control line may be arranged on the end of strips and shows a positive response when the analyte is diffused into the absorption pad 41b and may be used to verify tests using strips. The test results are considered valid, when the control line is positive.

The porous membrane 41c may be used in a flow through or lateral flow manner, which is known in the art. An analyte or a cleaning solution may be injected into the sample pad 41a. The flow through-type porous membrane may utilize strips wherein various tumor markers, disease markers or antibodies are immobilized on the porous membrane 41c. When the analyte is injected into the sample pad 41a, the analyte absorbed by the sample pad 41a is diffused throughout the porous membrane 41c by the capillary phenomenon and is thus biochemically specifically bonded to the capture antibody. The absorption pad 41b for promoting diffusion may be arranged on the terminal of the porous membrane 41c. Also, the conjugate pad may be selectively connected to the sample pad. In this case, the analyte injected into the sample pad is linked to the gold conjugate, the enzyme-linked antibody or the fluorescent material on the conjugate pad and the resulting complex is diffused into the porous membrane 41c.

When a cleaning solution is injected into the sample pad 41a, the cleaning solution absorbed in the sample pad 41a is diffused into the porous membrane 41c by capillary action to clean materials not bound to the capture antibody or non-specifically bound thereto and thereby remove background noise from the porous membrane 41c.

Figure 6:
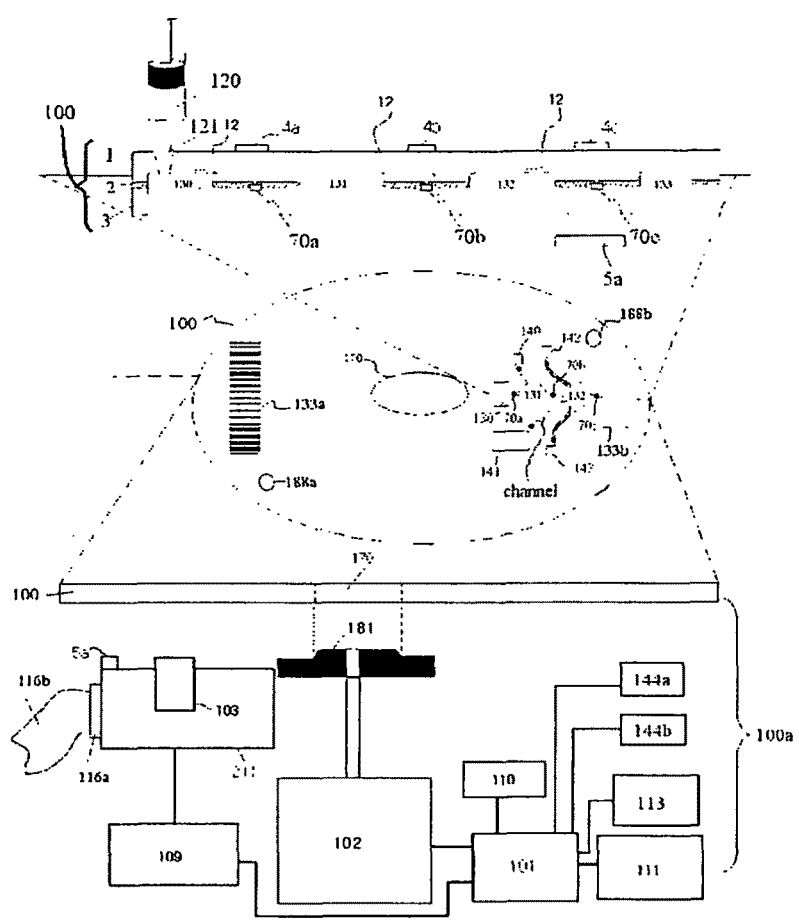
FIG. 6 is a sectional view illustrating a bio-disc reader to read a barcode and an assay site arranged on a bio-disc.

FIG. 6 is a sectional view illustrating a bio-disc reader 100a to read a barcode 133a printed or adhered onto the bio-disc 100 and an assay site 133b.

The bio-disc 100 has a structure in which a lab-on-a-chip is integrated in a thin-film body such as a conventional disc such as a CD or DVD. The body of the bio-disc 100 includes an upper base material 1, an intermediate base material 2 and a lower base material 3 which are laminated in this order. For example, chambers 130, 131, 132, 140, 141, 142 and 143 to store buffer solutions required for assay and to perform various chemical processes, channels to transfer fluids and buffer solutions, and valves 70a, 70b and 70c to control hole and closing of the channels may be integrated in the bio-disc 100. Reference numerals 4a, 4b, 4c are closing means of respective valves and Reference numeral 5a may be a permanent magnet which may be movable through the valve hole/closing means. In addition, the permanent magnet may provide a space-addressing means of the assay site 133b and the barcode 133a.

Reference numeral 188a is a thin-film circular magnet to space-address the barcode and reference numeral 188b is a thin-film circular magnet to space-address the assay sites.

Reference numeral 110 is an image sensor to read the assay sites 133b and the barcode 133a. Reference numerals 121 and 120 are a subject inlet and a subject inlet means, respectively. Reference numeral 12 is an outlet. Reference numeral 211 is a slider provided with the permanent magnet 5a and an optical pick-up device 103, which is connected to a slide motor 109 and operations thereof are thus controlled. The slider 211 may be provided with a permanent magnet 5a to space-address the barcode 133a and the assay site 133b and an optical pick-up device 103 to reproduce a conventional optical disc (CD or DVD). Reference numeral 144a is an illuminator to illuminate the image sensor 110 and reference numeral 144b is a UV generator to enable the barcode printed by a transparent UV fluorescent ink to be visible.

The space-addressing the barcode 133a or the assay site 133b on the bio-disc 100 may be carried out by the arrangement between the permanent magnet 5a and the thin-film circular magnets 188a and 188b through control of the slide motor 109 and the spindle motor 102. In this case, the image sensor 110 reads the barcode 133a or the assay site 133b. When the arrangement between the permanent magnet 5a and the thin-film circular magnet 188a is realized, the arrangement between the image sensor 110 and the barcode 133a is realized. When the arrangement between the permanent magnet 5a and the thin-film circular magnet 188b is realized, the arrangement between the image sensor 110 and the assay site 133b is realized.

The space-addressing may be accomplished by radial direction search and azimuthal direction search. In this case, the arrangement between the permanent magnet 5a and the thin-film circular magnets 188a and 188b is realized.

The radial direction search may be performed by control of the slide motor 109. The azimuthal direction search may be carried out by rotating the bio-disc 100 through rotation of the spindle motor 102 or control of a stepper motor, while stopping the slider 211. The stepper motor (not represented) may be selectively mounted on a gear present on the shaft of the spindle motor 102, when radial rotation of the bio-disc 100 is required.

Reference numeral 116b indicates a flexible cable to connect control signals required for the optical pick-up device 103 present on the slider 211, which is connected to a central control device 101 through a wafer or a harness 116a.

Reference numeral 181 is a turn table on which the bio-disc 100 is placed, and the bio-disc 100 is loaded in front of or on the top of the turn table through a central hole 170 of the bio-disc 100.

In one embodiment, the bio-disc reader 100a stores reading results of the barcode 133a or the assay sites 133b in a storage device 113 or transmits the same to the outside through an input/out device 111.

Figure 7:
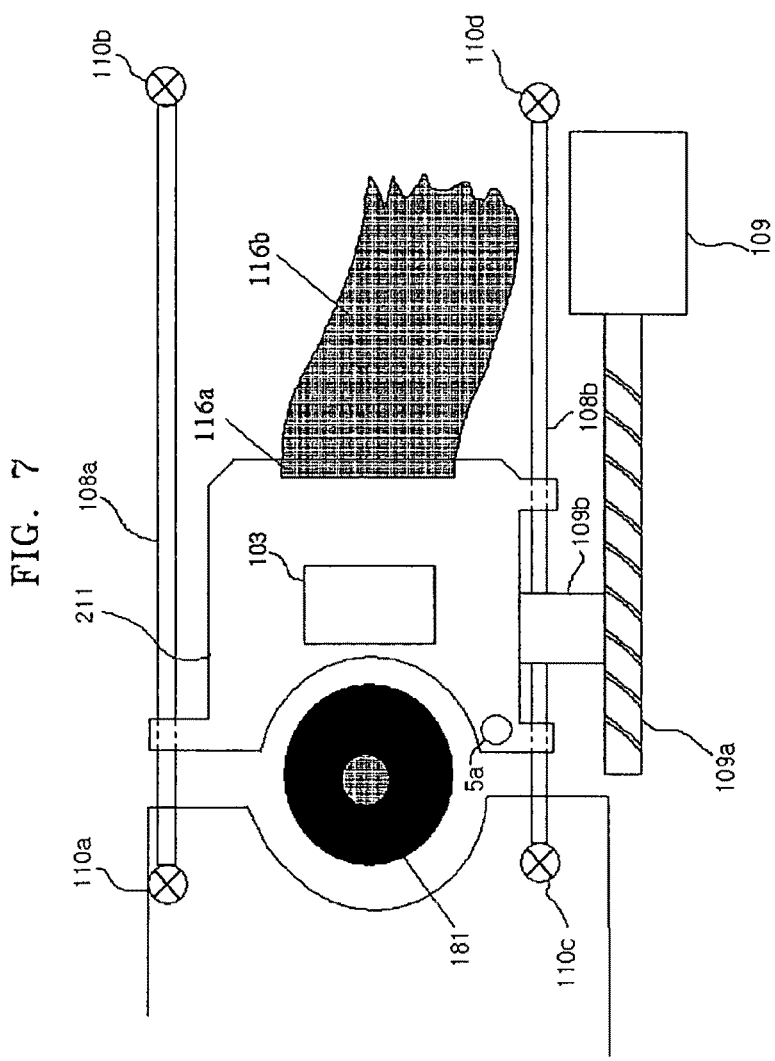
FIG. 7 is a top view illustrating a slider provided with a permanent magnet and an optical pick-up device according to one embodiment.

In one embodiment, the input/output device 111 may be a universal serial bus (USB) or IEEE1394 or ATAPI or SCSI or a device having a communication standard of internet network FIG. 7 is a top view illustrating a slider provided with a permanent magnet 5a and an optical pick-up device 103 according to one embodiment of the present invention.

The movement of the slider can be controlled by worm gear connections 109a and 109b connected to the shaft of a slide motor 109. The slider may slide using slide arms 108a and 108b as guides. The slide arms 108a and 108b are engaged through screws 110a, 110b, 110c and 110d on the body of the bio-disc reader (100a, shown in FIG. 1). Reference numeral 116b indicates a flexible cable, which is connected through a wafer or a harness 116a. Reference numeral 181 indicates a turn table rotated by the spindle motor (102, shown in FIG. 1).

Reference numeral 5a is a permanent magnet provided on the slider 211, which serves as a space-addressing means. The permanent magnet 5a may serve as a closing/hole means of the valve.

Figure 8:
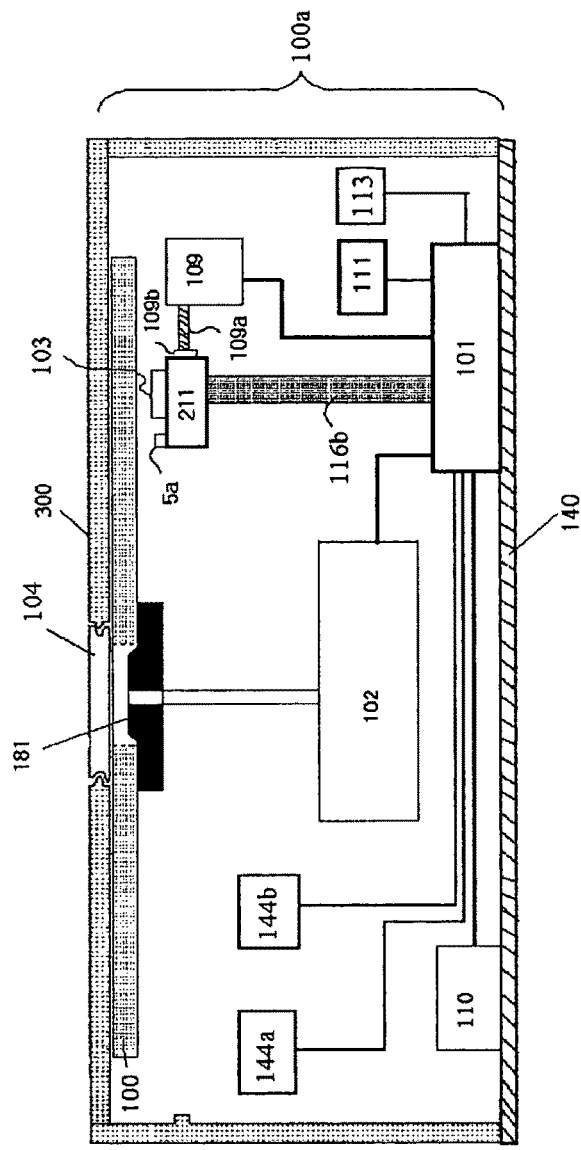
FIG. 8 is a side view illustrating a bio-disc reader 100a to operate and control the bio-disc.

FIG. 8 is a side view illustrating a bio-disc reader 100a to operate and control the bio-disc 100 of FIG. 1 according to one embodiment of the present invention.

Reference numeral 300 indicates a body to support the thin bio-disc reader 100a. A circuit substrate 140 is continuously engaged in the body 300 of the bio-disc reader under the bio-disc reader 100a, and the central control device 101 to control the bio-disc reader 100a, the illuminator 144a, the UV generator 144b, the storage device 113 and the input/output device 111 are arranged on the circuit substrate 140. The central control device 101 controls a spindle motor 102 to rotate and stop the bio-disc 100, controls movement of the optical pickup device 103 arranged on the slider 211 by control of the slide motor 109, and moves the permanent magnet 5a for space-addressing the assay site 132 of the bio-disc 100.

In addition, the central control device 101 decides whether the disc loaded on the bio-disc reader 100a is a conventional optical disc (for example, music CDs, CD-Rs, and game CDs/DVDs) or the bio-disc 100. That is, when the disc is a conventional optical disc, the device 101 transfers information read from the disc from the optical pick-up device 103 to the storage device 113 or input/output device 111, transfers data to be written to the optical pick-up device 103, or performs conventional operations for optical discs, for example, supplies various control signals required for reading and writing to respective elements, and when the disc is a bio-disc 100, the device 101 transfers command signals to control processes involved in the lap-on-a-chip to the respective elements.

In one embodiment, upon loading the bio-disc 100, the bio-disc reader 100a reads the barcode 133a to confirm validity, product information and product authentication of the bio-disc.

In one embodiment, in order to read the barcode 133a present on the bio-disc, the central control device 101 recognizes product identification (ID) of the bio-disc 100 and confirms that the disc loaded on the bio-disc reader 100a is a bio-disc.

In one embodiment, preferably, the image sensor 110 transfers reading results of the code 133a or the assay site 133b to the central control device 101 or the storage device 113 or the input/out device 111.

Reference numeral 104 is a compression device of the bio-disc 100 loaded on a turntable 181, which performs compression by means of attractive force, based on a magnetic field with the turntable 181 and is designed such that vertical movement and no-load rotation are allowed.

In one embodiment, the central control device 101 automatically ejects the bio-disc from the bio-disc reader 100a or sends a warning message to a user, when the loaded disc is considered to be a general optical disc (CD or DVD) or is an unusable bio-disc, based on the read barcode information.

In one embodiment, the detection of the assay site 133b using the image sensor 110 comprises treating the upper base material 1 with a non-transparent material or coating the same with a non-transparent paint to prevent light scattering from the illuminator 114a and noise caused by damage. In this case, for example, the transparency of the upper base material 1 may be 20 to 50%.

In one embodiment, the image sensor includes a line image sensor, a CCD or a CMOS for sensing light amount in pixel units. In one embodiment, the line image sensor includes a linear sensor array or a contact image sensor (CIS). The line image sensor is provided on the slider 211 and obtains one-dimensional images, while scanning the slider 211 in a radial direction, after space-addressing to obtain two-dimensional image information of the assay sites and barcodes.

The image sensor may be provided together with a light emission diode (LED) having a wavelength of 500 nm to 800 nm for light exposure on the slider 21.

Figure 9:
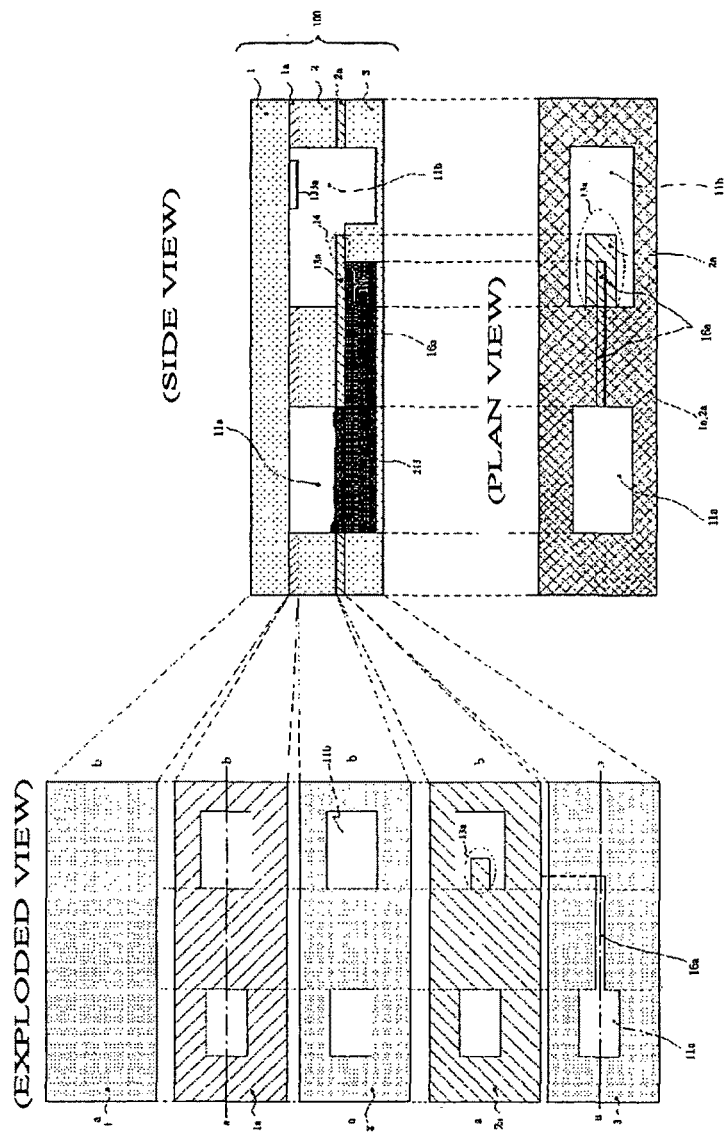
FIGS. 9 to 11 illustrate a bio-disc reader comprising the barcode printed or adhered to the barcode chamber and an ink chamber to store an ink to optically block the barcode according to one embodiment.
Figure 10:
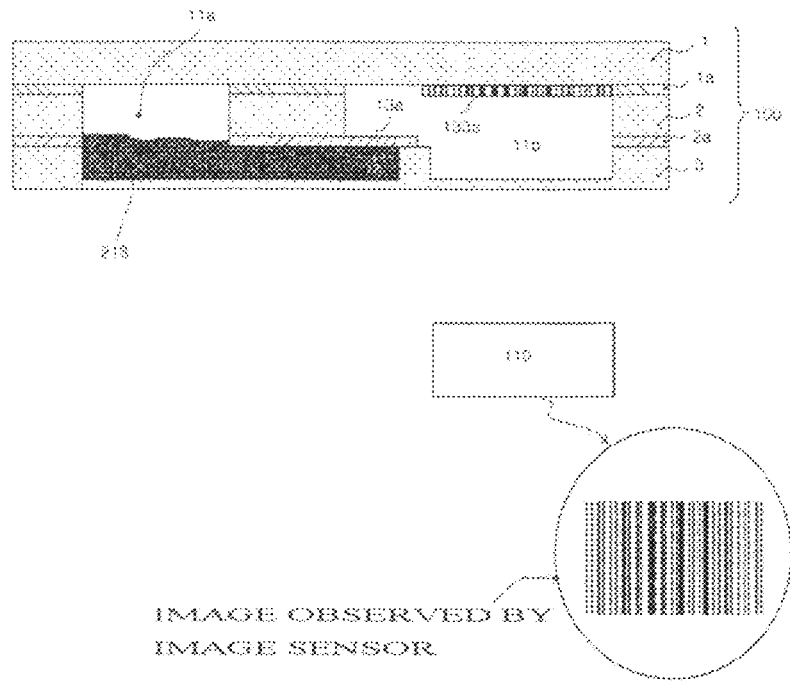
Figure 11:
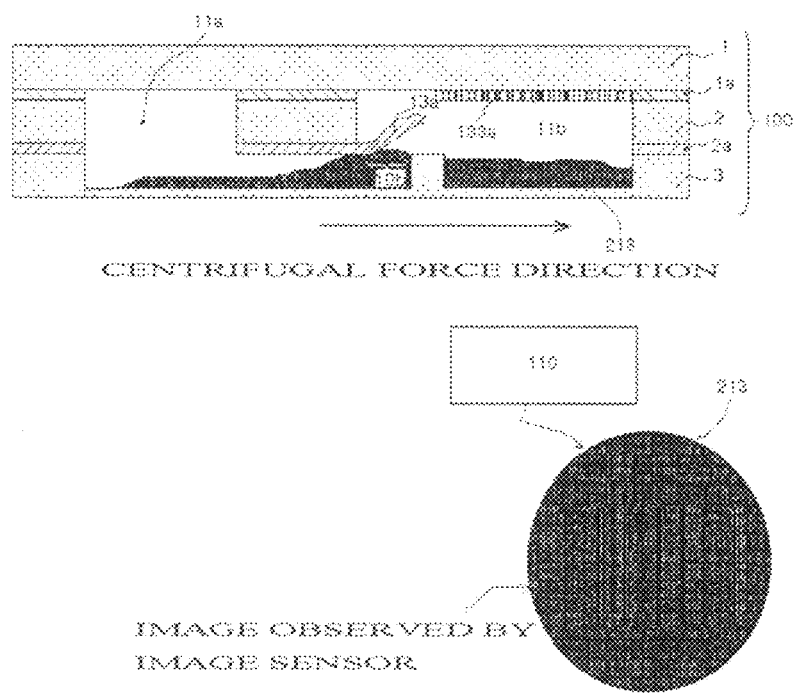

FIGS. 9 to 11 illustrate a bio-disc reader comprising the barcode 133a printed or adhered to the barcode chamber 11b and an ink chamber 11a to store an ink 213 to optically block the barcode 133a according to one embodiment. The ink may supply a distinguishing means to distinguish the assay sites from the barcode to the image sensor.

After the bio-disc reader completes recognition and reading of the barcode 133a, a hole blocking film 13a of the ink chamber 11a opens to flow the ink 213 to the barcode chamber 11b, and prevent the image sensor 110 from recognizing the barcode 133a upon reuse of the bio-disc. The ink 213 contains a fluorescent material, a black material or a transparent UV fluorescent material. When the ink is a black ink, information of the barcode 133a is blocked by the black ink and is thus entirely in black through the image sensor 110. Also, when the ink is a fluorescent material, information of the barcode 133a printed with the fluorescent material is blocked by the fluorescent material and the barcode cannot be recognized by the image sensor 110. In this case, the UV generator 144b is replaced by a laser generator to excite the fluorescent material and the image information of the fluorescent material excited by the image sensor 110 is thus obtained. In addition, when the ink is a transparent UV fluorescent material, information of the barcode 133a printed with the transparent UV fluorescent materials is blocked by the transparent UV fluorescent material and the image information of the UV fluorescent material excited by the image sensor 110 is thus obtained. Meanwhile, the UV generator 144b may be provided on the slider 211. For example, when a single-use bio-disc is used, or use thereof is completed and the bio-disc is then ejected, the barcode chamber 11b is filled with the ink to prevent the image sensor 110 from recognizing the barcode 133a.

The hole blocking film 13a may be a hydraulic burst valve which completely blocks a hole 10b by adhering a thin film adhesive tape to the hole and opens the hole 10b by releasing the thin film adhesive tape from an adhesion surface 14, based on a hydraulic force formed in the fluid by configuration force of the bio-disc 100.

The hydraulic burst valve may be provided in an hole interposed between the ink chamber and the barcode chamber, after recognition and reading of the barcode, to remove the hole blocking film 13a due to hydraulic pressure formed by the ink 213 stored in the ink chamber 11a caused by centrifugation force caused by rapid rotation of the bio-disc 100 and thus to open the hole 10b, to allow the ink 213 to move to the barcode chamber 11b, to optically block the barcode and thereby make the barcode unrecognizable.

FIG. 9 is an exploded view of a hydraulic burst valve using a thin film adhesive tape present in the body of the bio-disc 100 and a sectional view taken along the line a-b.

The body of the bio-disc 100 is composed of an upper base material 1, an intermediate base material 2, a lower base material 3; a passage 16a, allowing fluids to flow on the surface of base materials; an ink chamber 11a to store an ink solution; a barcode chamber 11b to print or adhere the barcode; and an hole 10b to connect the passage.

A barcode 133a is printed on or adhered to the bottom of the upper base material 1. The base materials 1, 2 and 3 are adhered to one another through the thin film adhesive tapes 1a and 2a to constitute a body of the bio-disc 100. Specifically, the base materials 1, 2 and 3 constitute the chambers 11a and 11b, the passage 16a is engraved to a predetermined depth in the lower base material 3, to connect the ink chamber 11a to the barcode chamber 11b, and the passage 16a is provided at the terminal thereof with the hole 10b to connect the ink chamber 11a to the barcode chamber 11b. The hole 10b is blocked by the hole blocking film 13a. The hole blocking film 13a is formed in the hole 10b using a thin film adhesive tape 2a, when the base materials 1, 2 and 3 are adhesion-assembled. The closing strength of the hole blocking film 13a may be proportional to the area of an adhesion surface 14 of the thin film adhesive tape 2a. For example, the hole 10b is blocked by the hole blocking film 13a for an expiration period, the barcode is recognized and read, and the hole blocking film 13a is removed due to hydraulic pressure formed by the ink 213 stored in the ink chamber 11a caused by centrifugation force induced by rapid rotation of the bio-disc 100 to open the hole 10b and thus to allow the ink 213 to move to the barcode chamber 11b. The hole blocking film 13a is flexible and is thus resistant to swelling and contraction caused by environmental factors such as temperature, thus avoiding ink evaporation and leakage caused by swelling and contraction of the body.

The hole blocking film 13a may be formed around the hole 10b, when the base materials 1, 2 and 3 are adhered to one another through the thin film adhesive tapes 1a and 2a and are assembled.

FIG. 10 illustrates a case in which the hole 10b is blocked by the hole blocking film 13a and the ink 213 is stored in the ink chamber 11a. In this case, the barcode 133a may be read by the image sensor 110.

FIG. 11 illustrates a state in which the hole blocking film 13a is removed by a hydraulic pressure derived from the ink 213 by rotation of the bio-disc 100 to open the hole 10b and thus to flow the ink 213 stored in the ink chamber 11a to the barcode chamber 11b. In this case, the barcode 133a is blocked by the ink 213 and cannot be read by the image sensor 110.

The thin film adhesive tape may include all adhesive tapes (gluing agents) including flexible one-sided tapes and two-sided tapes and the adhesive agent may be prepared from a material selected from the group consisting of silicon, rubbers, modified silicon, acrylic, polyester and epoxy.

The one-sided tapes or two-sided tapes are obtained by surface-treating one or both sides of release papers such as papers, vinyl polyester films, polyethylene films and other synthetic materials with an adhesive (or a gluing) agent. According to requirements, adhesive materials exhibiting properties such as superior sealing, buffering, vibration reduction, impact resistance, heat resistance, absorbent performance or adhesion force may be used.

In one embodiment, the hydraulic burst valve may be formed via thin film coating of on one side of a substrate by adhering an one-side tape to the substrate and removing a release paper therefrom, or printing a dispenser, spraying or silkscreen printing on one side of the substrate. That is, in one embodiment, the thin film adhesive tape may be coated on the substrate in the form of a thin film using an adhesive (gluing) agent without any release paper. The one-sided tape contains a hole blocking film 13a and the hole blocking film remains when the release paper is removed.

In one embodiment, thin-film coated substrates are adhered to one another through the adhesive agent to assemble a body of the bio-disc.

In one embodiment, when the bio-disc having the barcode blocked by the thin-film coated the ink is re-loaded, a user may be informed of the fact that the bio-disc is unsuitable for diagnosis or the bio-disc may be automatically ejected.

Figure 12:
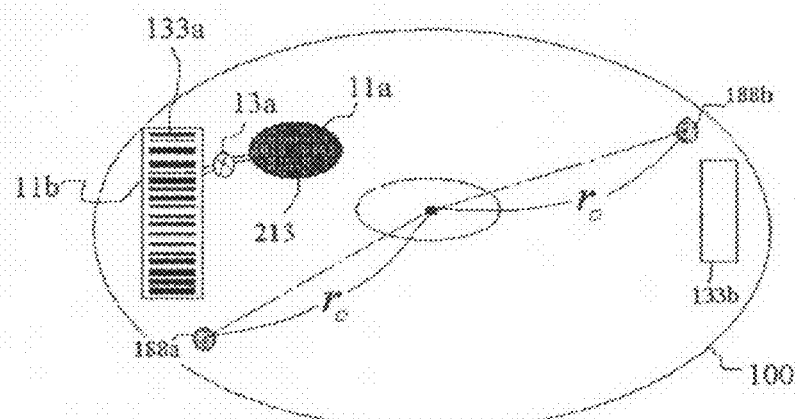
FIGS. 12 and 13 illustrate a distinguishing device realized by an ink chamber and a hydraulic burst valve according to FIGS. 9 to 11 according to one embodiment.
Figure 13:
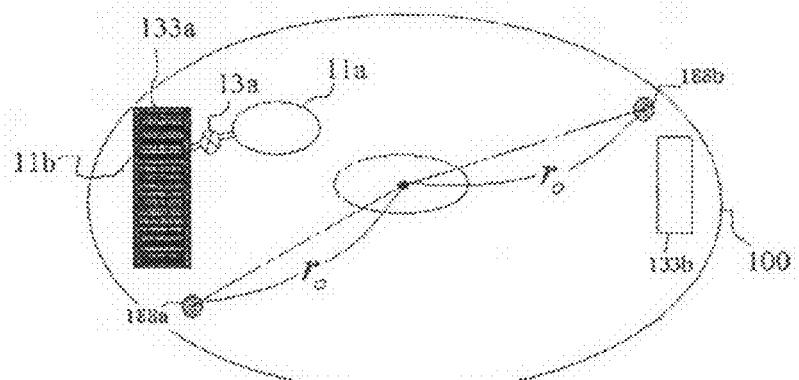
Figure 14:
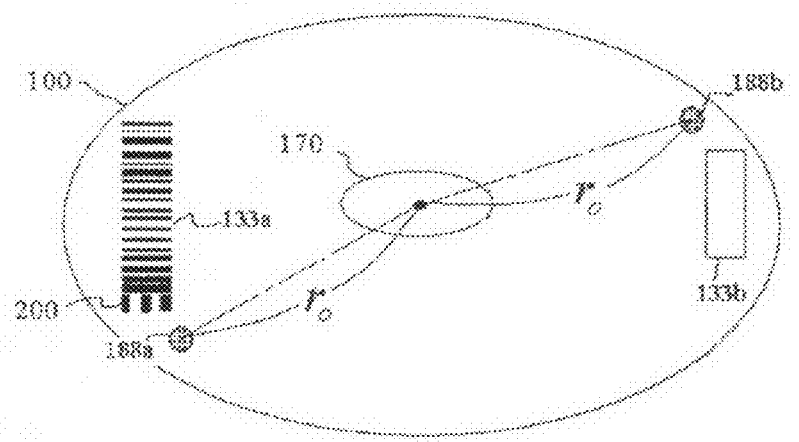
FIGS. 14 to 18 illustrate distinguishing devices to distinguish the barcode from the assay site using various barcode patterns according to exemplary embodiments.
Figure 15:
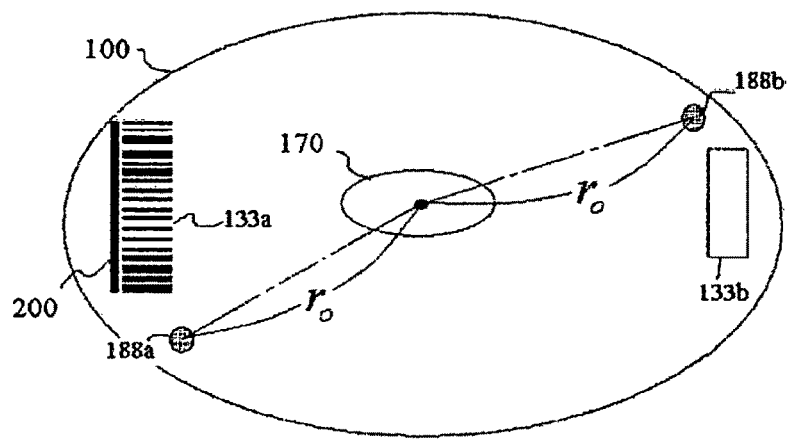
Figure 16:
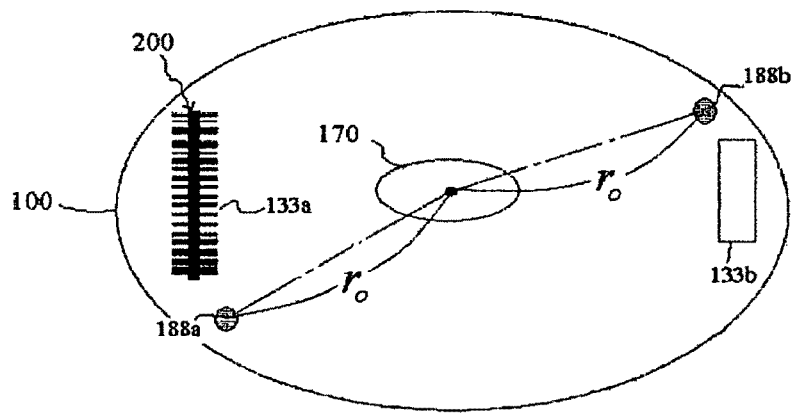
Figure 17:
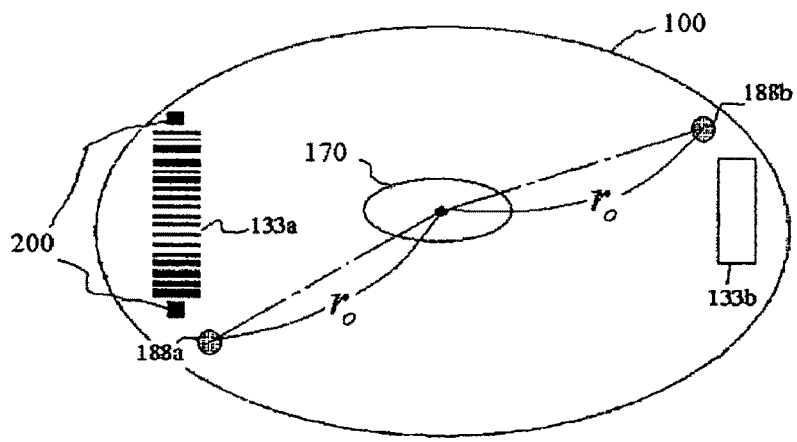

FIGS. 12 and 13 illustrate the distinguishing means realized by an ink chamber 11a and a hydraulic burst valve 13a of FIGS. 9 to 11 according to one embodiment.

The assay site 133b does not show any response, until the bio-disc 100 operates. In this case, the assay site 133b is white or transparent in color, but the barcode has an original barcode pattern. Accordingly, the assay site and the barcode can be distinguished from each other through the image sensor before the bio-disc operates (See FIG. 12). After the bio-disc completes operation, the barcode 133a is optically blocked by the ink 213 and is thus entirely black, thus being distinguished from the assay sites 133b (See FIG. 13). FIG. 12 shows a state in which the hole blocking film 13a is closed and FIG. 13 shows a state in which the hole blocking film 13a is opened.

FIGS. 14 to 18 illustrate a distinguishing means for distinguishing the barcode from the assay site using various barcode patterns according to exemplary embodiments.

In one embodiment, the various specific barcode patterns 200 may be distinguished with test lines or control lines of the assay sites. For example, specific barcode pattern 200 of a horizontal line pattern vertical to the test line and the control line may be further added to the barcode 133a. Hereinafter, the horizontal line pattern vertical to the test line and the control line will be referred to as a horizontal line pattern barcode 200. The horizontal barcode 200 may be a black or colored barcode.

Figure 18:
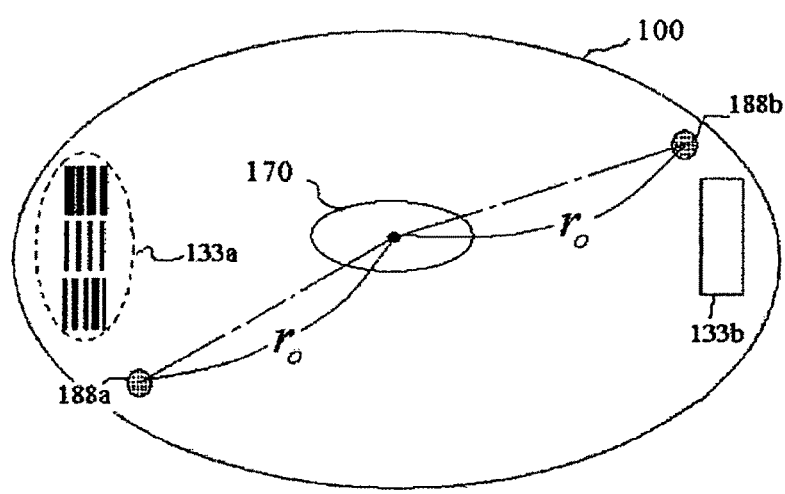

FIG. 18 shows a state in which the barcode 133a is composed of only a horizontal barcode according to one embodiment. In this case, the barcode may serve as a distinguishing means.

As shown in FIGS. 14 to 18, the thin-film circular magnet 188a for space-addressing the barcode 133a is arranged at coordinates (r0, θ1) of the bio-disc, and the thin-film circular magnet 188b for space-addressing the assay site 133b is arranged at coordinates (r0, θ2). The thin-film circular magnet 188a for space-addressing the barcode may be arranged in the same radius $r_0$ as the thin-film circular magnet 188b for space-addressing the assay site.

As apparent from the afore-going, the present invention provides a bio-disc reader to read assay sites and barcodes using a single image sensor to efficiently read product ID and assay sites. The bio-disc can read both assay sites and barcodes using one image sensor, thus being suitable for miniaturization of the bio-disc reader and product certification.

Although a few embodiments of the present invention have been shown and described, it would be appreciated by those skilled in the art that changes may be made in these embodiments without departing from the principles and spirit of the invention, the scope of which is defined in the claims and their equivalents.

What is claimed is:

1. A bio-disc comprising:
   one or more assay sites to assay a biomaterial and perform a biochemical reaction;
   a plurality of chambers to store fluids required for the biomaterial assay or the biochemical assay;
   a plurality of channels to connect the chambers to one another and allow fluids to flow;
   a body to integrate the assay sites, the channels and the chambers;
   a barcode printed on the body or adhered thereto;
   a first thin-film circular magnet provided on the body to space-address the barcode; and
   a second thin-film circular magnet provided on the body to space-address the body.

2. The bio-disc according to claim 1, wherein the first and second thin-film circular magnets are arranged on the same radius as the bio-disc.

3. The bio-disc according to claim 1, wherein the barcode is a colored one- or two-dimensional barcode, or a horizontal barcode.

4. The bio-disc according to claim 1, wherein the barcode contains information such as operating protocol, product ID and expiration date of the bio-disc, and the type of diseases to be assayed and diagnosed.

5. The bio-disc according to claim 1, wherein the barcode is printed by a fluorescent ink.

6. The bio-disc according to claim 5, wherein the fluorescent ink is a transparent UV fluorescent ink.

7. The bio-disc according to claim 1, further comprising a distinguishing device to distinguish the assay site from the barcode.

8. The bio-disc according to claim 7, wherein the distinguishing device is at least one selected from specific symbols, specific barcode patterns, specific color marks, specific holes, specific mechanical engravings, start characters and stop characters.

9. The bio-disc according to claim 8, wherein the specific barcode pattern is a horizontal barcode.

10. The bio-disc according to claim 1, further comprising:
    an ink chamber to store an ink to optically block the barcode;
    a barcode chamber including the barcode; and
    a hydraulic burst valve interposed between the ink chamber and the barcode chamber.

* * * * *